(12) United States Patent
Sandhu et al.

(10) Patent No.: US 10,368,920 B2
(45) Date of Patent: Aug. 6, 2019

(54) OCCIPITAL FIXATION ASSEMBLY, SYSTEM AND METHOD FOR ATTACHING THE SAME

(71) Applicant: K2M, Inc., Leesburg, VA (US)

(72) Inventors: Faheem Sandhu, Washington, DC (US); Kevin R. Strauss, Atlanta, GA (US); Larry McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 37 days.

(21) Appl. No.: 15/453,153

(22) Filed: Mar. 8, 2017

(65) Prior Publication Data

US 2017/0238972 A1    Aug. 24, 2017

Related U.S. Application Data

(62) Division of application No. 14/288,903, filed on May 28, 2014, now Pat. No. 9,597,122, which is a division
(Continued)

(51) Int. Cl.
*A61B 17/28* (2006.01)
*A61B 17/80* (2006.01)
(Continued)

(52) U.S. Cl.
CPC ........ *A61B 17/7055* (2013.01); *A61B 17/282* (2013.01); *A61B 17/7082* (2013.01);
(Continued)

(58) Field of Classification Search
CPC ............ A61B 17/7001; A61B 17/7047; A61B 17/7049; A61B 17/7055; A61B 17/7058; A61B 17/282; A61B 17/808
See application file for complete search history.

(56) References Cited

U.S. PATENT DOCUMENTS

| 1,390,485 A | 9/1921 | Bell |
| 3,019,887 A | 2/1962 | Lowden |

(Continued)

FOREIGN PATENT DOCUMENTS

WO    95/05782 A1    3/1995

OTHER PUBLICATIONS

Vijay K. Goel, PhD. et al. "Effects of Rigidity of an Internal Fixation Device", vol. 16, No. 3 Supplemental, 1991, pp. S155-S161.
(Continued)

*Primary Examiner* — Jacqueline T Johanas
(74) *Attorney, Agent, or Firm* — Lerner, David, Littenberg, Krumholz & Mentlik, LLP

(57) ABSTRACT

An occipital fixation assembly is provided. The occipital fixation assembly includes a first mounting plate configured for placement within a sinus cavity adjacent a rear portion of a skull of a patient. A threaded post extends from the first mounting plate. A coupling member includes an aperture configured to receive the threaded post therethrough. The coupling member includes an offset extension configured to support a surgical rod thereon. A fixation nut configured to threadably engage the threaded post of the first mounting plate is rotatable about the threaded post and translatable therealong. The fixation nut is rotatable with respect to the first mounting plate and the coupling member such that rotation of the fixation nut in a predetermined direction brings the first mounting plate and the coupling member toward one another and into secured engagement with the skull of a patient.

7 Claims, 12 Drawing Sheets

Related U.S. Application Data of application No. 12/904,613, filed on Oct. 14, 2010, now abandoned.

(60) Provisional application No. 61/278,925, filed on Oct. 14, 2009.

(51) Int. Cl.
*A61B 17/70* (2006.01)
*A61B 17/88* (2006.01)
*A61B 17/00* (2006.01)

(52) U.S. Cl.
CPC .......... *A61B 17/808* (2013.01); *A61B 17/809* (2013.01); *A61B 17/8872* (2013.01); *A61B 17/8875* (2013.01); *A61B 17/8888* (2013.01); *A61B 2017/00738* (2013.01)

(56) References Cited

U.S. PATENT DOCUMENTS

| | | |
|---|---|---|
| 3,997,138 A | 12/1976 | Crock et al. |
| 4,648,388 A | 3/1987 | Steffee |
| 4,743,260 A | 5/1988 | Burton |
| 5,024,213 A | 6/1991 | Asher et al. |
| 5,098,433 A | 3/1992 | Freedland |
| 5,127,912 A | 7/1992 | Ray et al. |
| 5,129,899 A | 7/1992 | Small et al. |
| 5,167,665 A | 12/1992 | McKinney |
| 5,234,432 A | 8/1993 | Brown |
| 5,250,049 A | 10/1993 | Michael |
| 5,257,994 A | 11/1993 | Lin |
| 5,269,784 A | 12/1993 | Mast |
| 5,312,404 A | 5/1994 | Asher et al. |
| 5,380,325 A | 1/1995 | Lahille et al. |
| 5,507,745 A | 4/1996 | Logroscino et al. |
| 5,545,164 A | 8/1996 | Howland |
| 5,545,228 A | 8/1996 | Kambin |
| 5,591,166 A | 1/1997 | Bernhardt et al. |
| 5,649,926 A | 7/1997 | Howland |
| 5,653,708 A | 8/1997 | Howland |
| 5,713,898 A | 2/1998 | Stucker et al. |
| 5,722,976 A | 3/1998 | Brown |
| 5,947,968 A | 9/1999 | Rogozinski |
| 6,039,738 A | 3/2000 | Sanders et al. |
| 6,059,786 A | 5/2000 | Jackson |
| 6,083,224 A | 7/2000 | Gertzbein et al. |
| 6,146,384 A | 11/2000 | Lee et al. |
| 6,287,308 B1 | 9/2001 | Betz et al. |
| 6,682,532 B2 | 1/2004 | Johnson et al. |
| 6,755,834 B2 | 6/2004 | Amis |
| 7,048,737 B2 | 5/2006 | Wellisz et al. |
| 7,303,563 B2 | 12/2007 | Poyner et al. |
| 9,327,069 B2 | 5/2016 | Foster et al. |
| 9,597,122 B2 | 3/2017 | Sandhu et al. |
| 2001/0011173 A1 | 8/2001 | Lerch |
| 2004/0127908 A1 | 7/2004 | Roman et al. |
| 2005/0070899 A1 | 3/2005 | Doubler et al. |
| 2005/0080417 A1 | 4/2005 | Alexis et al. |
| 2005/0137594 A1 | 6/2005 | Doubler et al. |
| 2005/0256510 A1 | 11/2005 | Moskowitz et al. |
| 2006/0247628 A1 | 11/2006 | Rawlins et al. |
| 2006/0264932 A1 | 11/2006 | Bert |
| 2008/0103502 A1* | 5/2008 | Capote ............... A61B 17/7007 606/257 |
| 2008/0281359 A1 | 11/2008 | Abdou |
| 2009/0030463 A1 | 1/2009 | Samudrala et al. |

OTHER PUBLICATIONS

Rolando M. Puno, MD, et al. "Biochemical Analysis of Transpedicular Rod Systems", vol. 16, No. 8, 1991, pp. 973-980.
James Zucherman, MD, et al. "Early Results of Spinal Fusion Using Variable Spine Plating Systems", vol. 13, No. 5, 1988, pp. 570-579.
Faheem A. Sandhu, MD, PhD. et al. "Occipitocervical Fusion for Rheumatoid Arthritis Using the Inside-Outside Stabilization Technique", vol. 28, No. 4, 2003, pp. 414-419.

\* cited by examiner

OCCIPITAL FIXATION ASSEMBLY, SYSTEM AND METHOD FOR ATTACHING THE SAME

CROSS-REFERENCE TO RELATED APPLICATIONS

The present application is a division of U.S. patent application Ser. No. 14/288,903, filed on May 28, 2014, which is a division of U.S. patent application Ser. No. 12/904,613 filed on Oct. 14, 2010, which has been abandoned, which claims the benefit of and priority to U.S. Provisional Application No. 61/278,925 to Sandhu et al., filed on Oct. 14, 2009, the entire contents of each of which are incorporated by reference herein.

BACKGROUND

Technical Field

The present disclosure relates to an occipital fixation assembly, system and method for attaching the same. More particularly, the present disclosure relates to an occipital fixation assembly that is configured to support a surgical implant thereon and securely anchor to an inside of a skull of a patient.

Description of Related Art

As is commonly known in the art, an occipitocervical junction includes an occiput, atlas and axis. The occipitocervical junction is a unique interface between the cranium and cervical spine. More than 50% of the rotation and flexion-extension are provided from this region. Ligaments in this region must resist forces about all six degrees of freedom. Moreover, instrumentation constructs not only must resist forces in all of these vectors, but also must resist the significant moment created by the suboccipital bone and the cervical spine, which meet at a 50° angle. Any instrumentation construct designed for use in this region must, therefore, have adequate geometry to interface with the osseous structures of the spinal structures as well as have sufficient rigidity and purchase to resist these forces until bone fusion can occur.

At one time, occipitocervical instability and lesions located at the occipitocervical junction were considered inoperable and terminal. Since the first description of an occipitocervical fusion, multiple methods of fusion in this region have been described. Descriptions of simple bone grafts with halo immobilization; wire, pin, or hook constructs; rigid metallic loops and rectangles fixed to the bone with either screws or wires; and most recently, plate or rod constructs with screws have all been described. In general the evolution of this technology has focused on providing increasingly more rigid constructs to facilitate bone fusion and to minimize the need for and duration of external immobilization.

A common technique for fixing occipitocervical instability is the use of an inverted Y-shaped screw plate. Using this technique, the plate is secured to C1-2 with transarticular screws and to the suboccipital bone with paramedian screws; the suboccipital bone varies in thickness, with a mean thickness of 14 mm. Screws must be carefully selected to provide adequate purchase, yet avoid cerebella injury. Utilizing the maximum screw length possible is critical because shorter screws have decreased resistance to pullout. If stabilization is required below the C1-2 level, then lateral mass screws can be placed through additional holes in a longer plate to include these levels as well. In certain instances, a bone graft may be added to promote fusion. The Y-shaped plate, in combination with transarticular screws, is an economical alternative. Immediate postoperative stabilization is achieved and very low rates of pseudarthrosis have been reported. Due to the risk of selecting the correct screw size and the potential for cerebellar injury along with the potential for screw pull-out due to the short nature of the screw lengths allowed for use, it may prove advantageous to provide an occipital fixation assembly, and a system and method for attaching the same that can reduce the chance for pull-out and reduce the risk for cerebellar injury.

SUMMARY

The present disclosure provides an occipital fixation assembly. The occipital fixation assembly includes a first mounting plate configured for placement within a sinus cavity adjacent a rear portion of a skull of a patient. A threaded post extends from the first mounting plate. A coupling member includes an aperture configured to receive the threaded post therethrough and an offset extension configured to support a surgical rod thereon. A fixation nut, configured to threadably engage the threaded post of the first mounting plate, is rotatable about the threaded post and translatable therealong. The fixation nut is rotatable with respect to the first mounting plate and the coupling member such that rotation of the fixation nut in a predetermined direction brings the first mounting plate and the coupling member toward one another and into secured engagement with the skull of a patient.

The present disclosure provides an occipital fixation system or system for attaching an occipital fixation assembly to a patient for subsequent attachment of a surgical rod thereto. The system includes a first mounting plate configured for placement within a sinus cavity adjacent a rear portion of a skull of a patient. The first mounting plate has a threaded post that extends therefrom. A coupling member includes an aperture configured to receive the threaded post therethrough. An offset extension disposed in parallel orientation with respect to the threaded post is configured to support a surgical rod thereon. A fixation nut configured to threadably engage the threaded post is rotatable about the threaded post and translatable therealong. The fixation nut is rotatable with respect to the first mounting plate and the coupling member such that rotation of the fixation nut in a predetermined direction brings the first mounting plate and the coupling member toward one another and into secured engagement with the skull of a patient. A forceps is configured to grasp a portion of the threaded post when the threaded post has been inserted through an aperture that has been previously drilled in the sinus cavity. A wrench assembly is adapted to engage and, subsequently, rotate the fixation nut about the threaded post.

The present disclosure also provides a method for attaching an occipital fixation assembly to a patient for subsequent attachment of a surgical rod thereto. The method includes creating an aperture within a sinus cavity adjacent a rear portion of a skull of a patient. A threaded post of a first mounting plate of an occipital fixation assembly is, subsequently, positioned through the aperture created within the sinus cavity. Thereafter, a coupling member of the occipital fixation assembly is attached to the threaded post of the first mounting plate. A fixation nut is then positioned about the threaded post and, subsequently, rotated in a predetermined direction about the threaded post such that the first mounting plate and the coupling member move toward one another and into secured engagement with the skull of a patient. A surgical rod is coupled to the coupling member.

BRIEF DESCRIPTION OF THE DRAWINGS

Various embodiments of the present disclosure are described herein with reference to the drawings wherein.

DETAILED DESCRIPTION

In the following description, as is traditional, the term "proximal" refers to a portion of a surgical instrument closer to the operator while the term "distal" refers to a portion of a surgical instrument farther from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Figure 1:
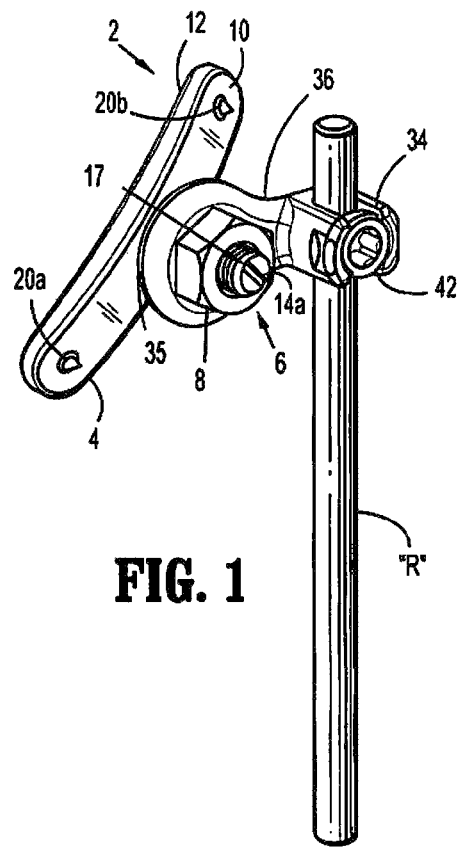
FIG. 1 is a perspective view of an occipital fixation assembly with a surgical rod secured thereon according to an embodiment of the present disclosure.

With reference to FIGS. 1-7C, and initially with reference to FIG. 1, an occipital fixation assembly 2 is illustrated. The occipital fixation assembly 2 is positionable within a sinus cavity adjacent a rear portion of the skull, lateral to a brain stem region, i.e., adjacent the occiput. To this end, the occipital fixation assembly 2 includes a first mounting plate 4, a coupling member 6 and a fixation nut 8.

Continuing with reference to FIG. 1, the mounting plate 4 is illustrated. Mounting plate 4 includes a generally elongated configuration having top and bottom surfaces 10 and 12, respectively. In the illustrated embodiments, the mounting plate 4 includes a slight curvature or concavity "C" (see FIG. 2 for example) that is configured to follow a contour of the occiput of a skull. As can be appreciated, this curvature or concavity facilitates anchoring the mounting plate 4 to the occiput.

One or more barbs (two barbs 20a and 20b are shown in the drawings) are operably disposed on the top surface 10 of the mounting plate 4 (FIG. 1). Barbs 20a and 20b are configured to facilitate anchoring the mounting plate 4 into an interior surface of the skull of a patient and to minimize rotation of the mounting plate 4 when the fixation nut 8 is rotated about a threaded post 14a (FIGS. 1-5) or movement of the mounting plate 4 when installed in the occiput. The barbs 20a and 20b include a generally conical configuration with a substantially pointed tip.

In one particular embodiment, to facilitate fixation of the mounting plate 4 to an interior surface of a skull, the barbs 20a and 20b may reside in generally circumferential recesses 21a and 21b, respectively, see FIGS. 5-7C. The recesses 21a and 21b are configured to engage soft tissue that may be disposed adjacent the interior surface of the skull. The barbs 20a and 20b are set into the recesses 21a and 21b at a depth that allows a majority of a surface area of the barbs 20a and 20b to sufficiently anchor into the interior surface of the skull.

Figure 3:
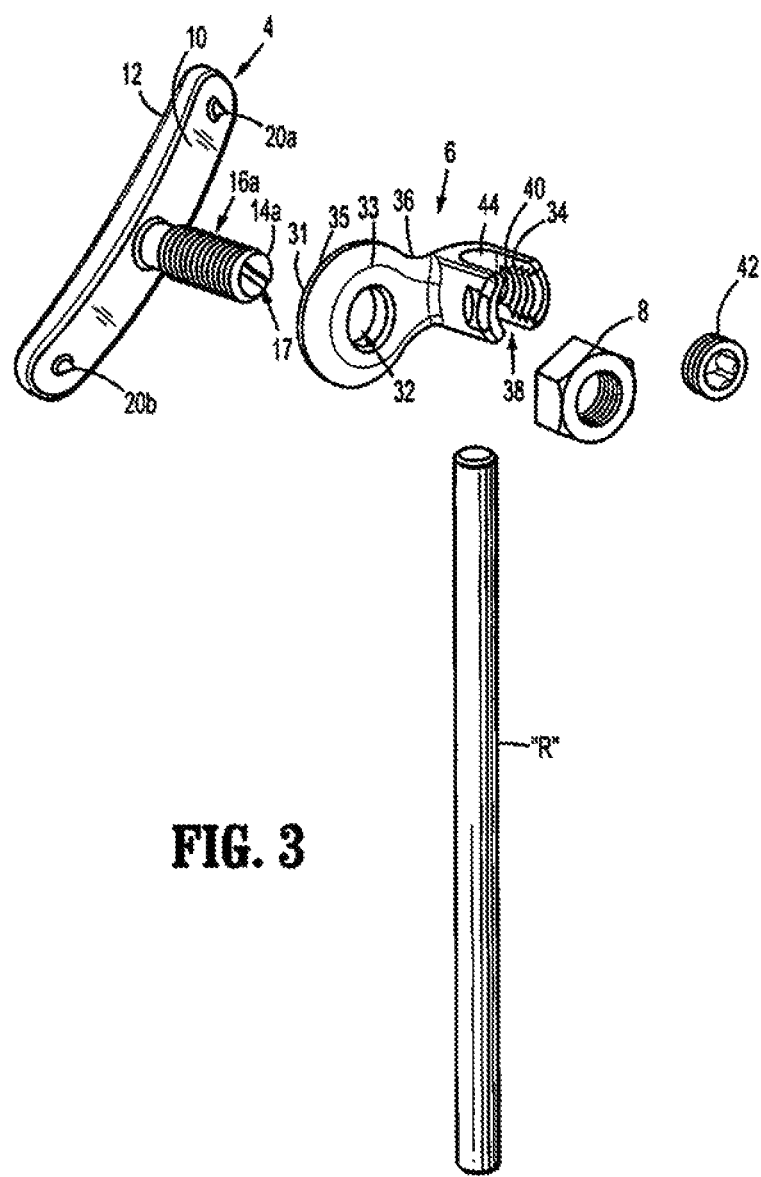
FIG. 3 is an exploded view of the occipital fixation assembly depicted in FIG. 1 with components separated.

With reference again to FIG. 1, the elongated post 14a extends in a generally orthogonal orientation from the top surface 10 such that the mounting plate 4 has a generally "T" shape (FIG. 3). The elongated post 14a may be monolithically formed with the mounting plate 4 or may be coupled to the mounting plate 4 by one or more suitable coupling methods, e.g., welded to the top surface 10 of the mounting plate 4. In the illustrated embodiments, the elongated post 14a is monolithically formed with the mounting plate 4.

Figure 2:
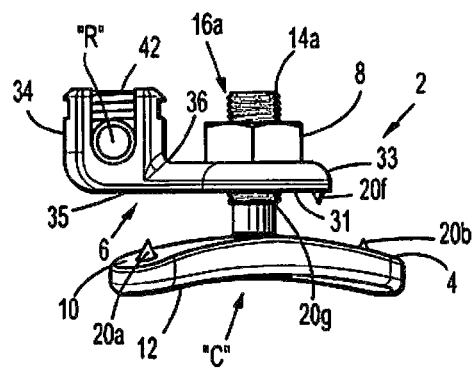
FIG. 2 is a front view of the occipital fixation assembly depicted in FIG. 1.

A plurality of threads 16a extends along an outer circumferential surface of the elongated post 14a. The plurality of threads 16a extends along a majority of a length of the elongated post such that a portion of the elongated post 14a adjacent the top surface 10 of the mounting plate 4 is devoid of the plurality of threads 16a (FIGS. 2 and 3). This portion of the elongated post devoid of the plurality of threads 16a serves as a relief for cutting the plurality of threads 16a. Moreover, this portion of the elongated post 16a devoid of the plurality of threads allows a mountng plate 5 to be threaded over the threaded post 16a until the mounting plate 5 passes the plurality of threads 16a where it can be rotated 360° (see FIG. 7A in combination with FIG. 7B) without advancing in or out of the occiput when being deployed into a final position (FIG. 7C), described in greater detail below. In certain instances, this portion of the elongated post devoid of the plurality of threads is intended to prevent "overtightening" of the coupling member 6 to the elongated post 14a.

In the embodiment illustrated in FIGS. 1-7C, a proximal end of the threaded post 14a includes a slot 17 (FIGS. 1 and 3) that is configured to receive a working end of a driving device, e.g., a screwdriver (or the like), that is configured to rotate the mounting plate 4 with respect to the fixation nut 8 when the fixation nut 8 is positioned on the threaded post 14*a*. The driving tool may include a blade configured for receipt in the slot 17 for holding the mounting plate 4 in a desired orientation while the fixation nut 8 is rotated about the threaded post 14*a*. Additionally, the slot 17 turns the threaded post 14*a* (and, thus, the mounting plate 4) after the mounting plate 5 is pulled and set to the inside surface of the occiput (with barbs 20*c* and 20*d*) to the final deployed cross position (FIG. 7C), described in greater detail below.

Continuing with reference to FIG. 1, the coupling member 6 is illustrated. Coupling member 6 is configured to operably couple to the mounting plate 4 (or, in some instances, to mounting plate 4 and a second mounting plate 5, see FIGS. 5-7C) and to engage an exterior surface of a skull. To these ends, coupling member 6 includes a base member 36.

Base 36 includes a generally annular configuration defined by an outer peripheral wall 35 that joins respective bottom and top surfaces 31 and 33 (FIGS. 1-4) to each other. Bottom surface 31 includes one or more barbs, e.g., three barbs 20*e*-20*g*, disposed thereon (see FIG. 2 in combination with FIG. 4) that are configured in a manner as described above with respect to barbs 20*a*-20*b*. However, unlike barbs 20*a*-20*b* that are configured to anchor into an interior surface of the skull, barbs 20*e*-20*g* are configured to anchor to an exterior surface of the skull. Top surface 33 is configured to support the fixation nut 8 thereon. An aperture 32 (FIGS. 3 and 4) extends from the top surface 33 to the bottom surface 31 and is configured to receive the threaded post 14*a* (or in certain embodiments, a threaded post 14*b*, described in greater detail below) and a portion of the fixation nut 8 therethrough.

Coupling member 6 is also configured to support the surgical rod "R" thereon (FIG. 1). To this end, coupling member 6 includes an offset extension 34 (FIGS. 1-4).

Figure 4:
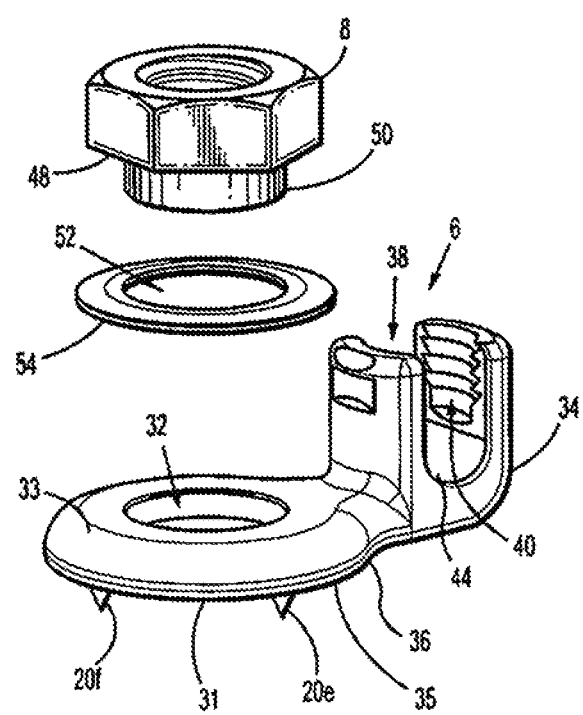
FIG. 4 is an exploded view of a coupling member associated with the occipital fixation assembly depicted in FIG. 1.
Figure 5:
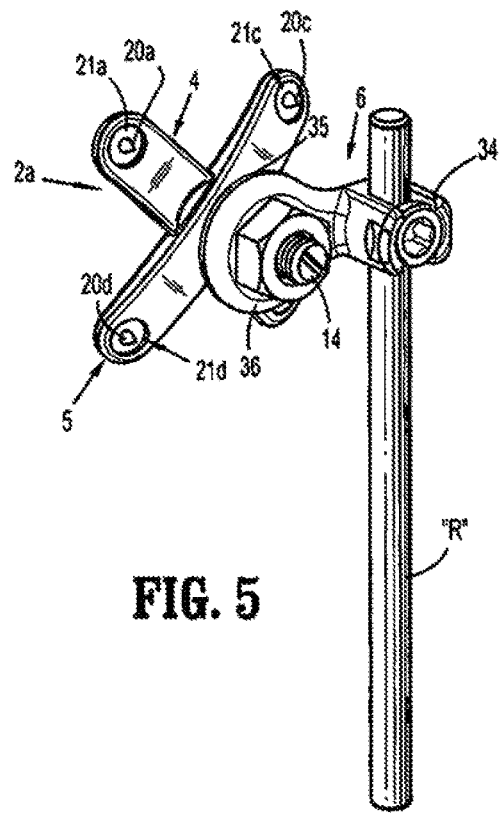
FIG. 5 is a perspective view of an alternative configuration of the occipital fixation assembly depicted in FIG. 1.
Figure 6:
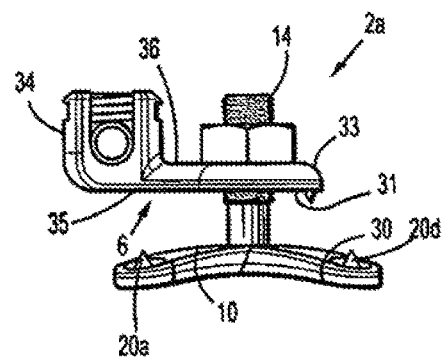
FIG. 6 is a front view of the occipital fixation assembly depicted in FIG. 5.

Offset extension 34 is disposed in parallel orientation with respect to the threaded post 14*a* (or in some embodiments with respect to the threaded post 14*b*), see FIGS. 1-3 and 5-7. The offset extension 34 includes a generally elongated slot 38 (FIGS. 3 and 4) having an intermittent threaded portion 40 (FIGS. 3 and 4 show one half of the intermittent threaded portion 40) configured to receive a set-screw 42 (FIGS. 1-3) therein and a non-threaded portion 44 (FIGS. 3 and 4) configured to receive the surgical rod "R" therein (FIGS. 1 and 2). The threaded and non-threaded portions, 40 and 44, respectively, of the offset extension 34 are arranged such that when the surgical rod "R" is secured thereto, the surgical rod "R" is oriented perpendicular to the set-screw 42 (FIGS. 1 and 2).

With reference again to FIG. 1, the fixation nut 8 is shown. Fixation nut 8 is configured to threadably engage the threaded post 14*a* of the mounting plate 4 (or in some instances threaded post 14*b* (FIG. 8A)). Fixation nut 8 is rotatable about the threaded post 14*a* and translatable therealong. Moreover, fixation nut 8 is rotatable with respect to the mounting plate 4 and the coupling member 6 such that rotation of the fixation nut 8 in a predetermined direction, e.g., a clockwise direction, brings the mounting plate 4 and the coupling member 6 toward one another and into secured engagement with the skull of a patient.

Preferably, a bottom surface 48 of the fixation nut 8 includes a generally elongated extension 50 that is configured to extend into an aperture 52 of a washer 54 and the aperture 32 of the base 36 (FIG. 4). The extension 50 is configured to facilitate positioning the fixation nut 8 about the threaded post 14*a* (or threaded post 14*b*) and the washer 54 distributes or "spreads" a load of the fixation nut 8 evenly across the top surface 33 of the base member 36 when the fixation nut is rotated about the threaded post 14*a*. In the embodiment illustrated in FIG. 4, the washer 56 has a generally conical shape and is also intended to serve as a lock washer. While the fixation nut 8 and washer 56 have been described herein as two separate components that couple to the coupling member 6, it is within the purview of the present disclosure that the coupling member 6, fixation nut 8 and washer 56 may be formed as one integral component.

Figure 7A:
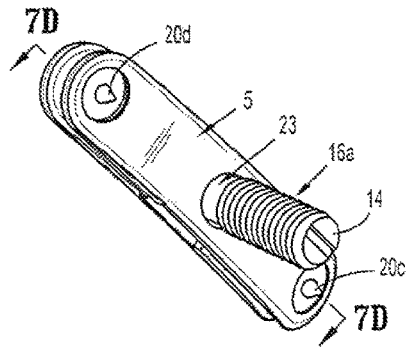
FIGS. 7A-7C are perspective views illustrating a mounting plate of the occipital fixation assembly depicted in FIG. 5 with the mounting plate shown in various configurations.
Figure 7B:
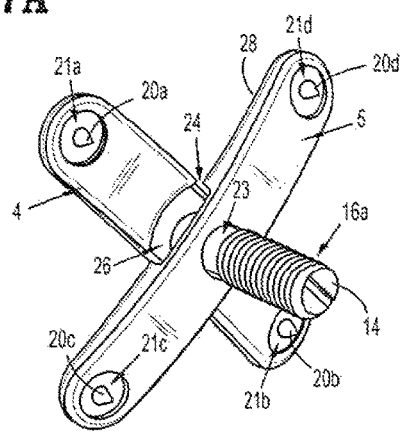
Figure 7C:
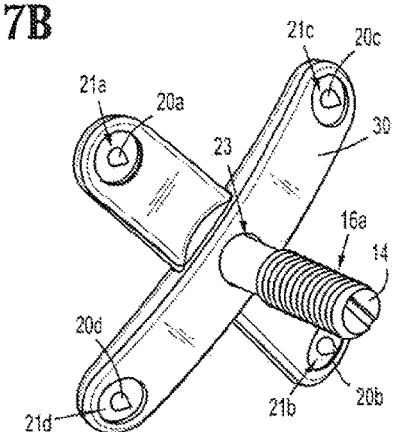

To facilitate fixation of occipital fixation assembly 2*a* to an interior surface of a skull, a second mounting plate 5 may be operably coupled to the mounting plate 4, see FIGS. 5-7C. To this end, the mounting plate 5 includes an opening 23 of suitable dimension, see FIGS. 7A-7C. More particularly, the opening 23 includes an outer diameter that is less than an outer diameter defined by an outer edge of the plurality of threads 16*a*. The mounting plate 5 is rotatable about the threaded post 14*a* such that the mounting plate 5 may be rotated from a first position, e.g., a "nested position," (FIGS. 7A and 7D) that is conducive for positioning the mounting plates 4 and 5 adjacent to an interior surface of a skull, to a subsequent or anchoring position (FIGS. 7B-7C) that is conducive for securing or lagging the mounting plates 4 and 5 to the interior surface of a skull. In the anchoring position, the mounting plates 4 and 5 may be disposed transverse to each other and form a generally crisscross or "X" shape or configuration, as best seen in FIG. 7C.

Mounting plate 5 includes one or more barbs, e.g., barbs 20*c* and 20*d*, disposed on a top surface 30 thereof. As described above with respect to barbs 20*a* and 20*b*, barbs 20*c* and 20*d* may reside in corresponding recesses 21*c* and 21*d*, respectively, see FIGS. 5-7C).

To facilitate positioning the mounting plates 4 and 5 inside the occiput, a bottom surface 28 of the mounting plate 5 includes a pair of indents 25*a* and 25*b* that are configured to releasably engage the barbs 20*a* and 20*b* (FIG. 7D); the indents 25*a* and 25*b* are shown engaged with the barbs 20*a* and 20*b*, respectively and, as a result thereof, are not explicitly shown. In the "nested" position, the mounting plate 5 and the mounting plate 4 can be inserted together into an aperture or slot in the occiput and rotated together until a final position, e.g., an anchored position, is achieved for the mounting plate 5, which can be seated or anchored into the occiput by pulling the nested mounting plates 4 and 5 so that the barbs 20*c* and 20*d* on the mounting plate 5 "dig" into the inside of the occiput. Subsequently, the mounting plate 4 can be deployed to the final (cross) position (FIG. 7C) using the slot 17 in the end of the threaded bolt. More particularly, the operable end of a screwdriver may be utilized to engage the slot 17 and, subsequently, turn the mounting plate 4 that disengages the barbs 20*a* and 20*b* from the respective indents 25*a* and 25*b*. The barbs 20*a* and 20*b* on the mounting plate 4 may then be brought into contact with the inside of the occiput, thus, fixing both mounting plates 4 and 5 in place.

Figure 7D:
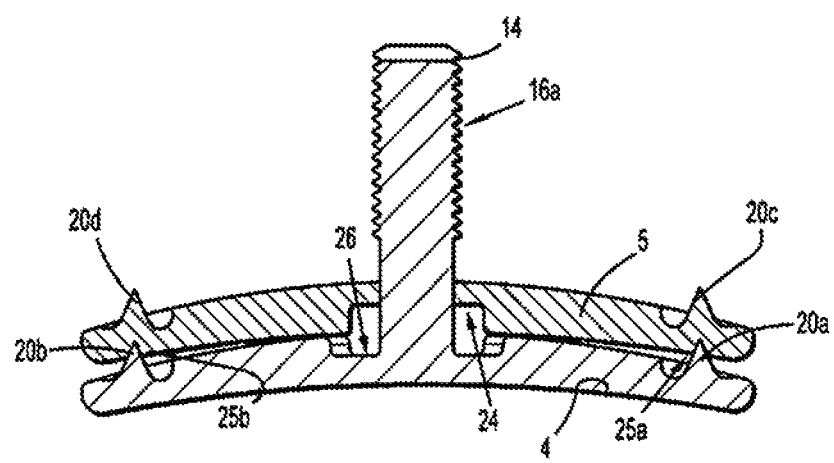
FIG. 7D is a cross-sectional view of the mounting plate depicted in the configuration of FIG. 7A taken along section line 7D-7D.

To facilitate anchoring the mounting plates 4 and 5 into the interior surface of a skull, a bottom surface 28 of the mounting plate 5 includes a notched portion 24 that is configured to receive and/or mate with a portion, e.g., a corresponding notched portion 26 disposed on the top surface 10, of the mounting plate 4 (FIGS. 7B and 7D). In the anchored position, the notched portions 24 and 26 enable the top surface 10 of the mounting plate and top surface 30 of the mounting plate 5 to be flush with each other, as best seen in FIG. 7D; this provides a substantially uniform contact surface between the mounting plates 4 and 5 and the interior surface of the skull. This substantially uniform contact surface facilitates positioning the barbs 20a-20d adjacent to the interior surface of the skull, which, in turn, ensures that the barbs 20a-20d properly engage the interior surface of skull. As can be appreciated, having all the barbs 20a-20d properly engaged to the interior surface of the skull reduces and/or eliminates the likelihood of inadvertent movement of the mounting plates 4 and 5 after the occipital fixation assembly 2a has been affixed to the interior surface of the skull.

In use, an aperture is, initially, created within a sinus cavity adjacent a rear portion of a skull of a patient, i.e., adjacent the occiput. For purposes herein, the aperture may be created utilizing one or more suitable surgical devices, e.g., a surgical drill.

Figure 13:
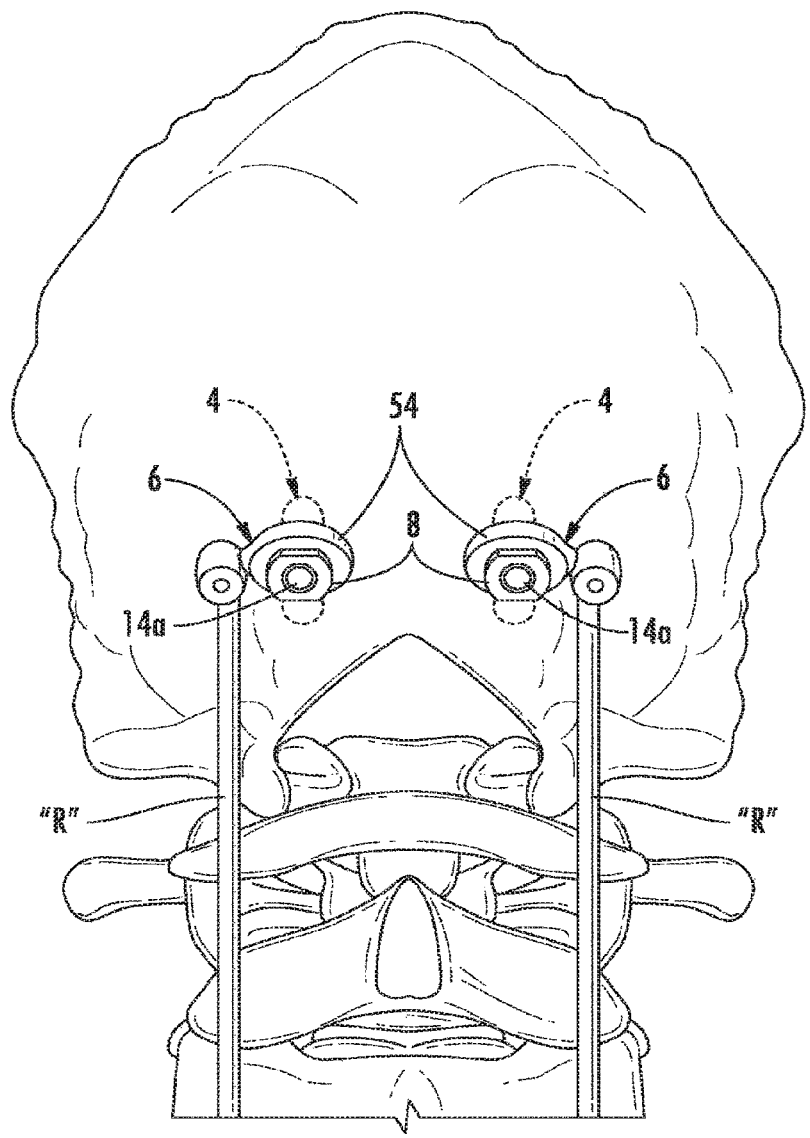
FIG. 13 is a rear view of the occipital fixation assembly depicted in FIG. 1 with the mounting plate shown being inserted within an occipital sinus cavity of a patient.

Mounting plate 4 is positioned through the aperture created within the sinus cavity adjacent the occiput. Thereafter, coupling member 6 is positioned about the threaded post 14a (see FIG. 1 in combination with FIG. 3). In particular, with additional reference to FIG. 13, once the physician creates the desired opening in the patient's skull, one end of the mounting plate 4 is inserted through the opening until the opposing end clears the surface of the skull and can be positioned beneath the surface of the skull. Subsequently, the mounting plate 4 is moved in a generally opposing direction such that the entire mounting plate 4 is disposed beneath the surface of the skull (i.e. on the inside). Once positioned, the threaded post 14a extends through the opening. This installation technique is applicable to all disclosed embodiments of the occipital fixation assembly. As will be appreciated, the opening will have a dimension that is slightly greater than the dimensions of the mounting plate 4.

The fixation nut 8 including the washer 54 is positioned about the threaded post 14a and over the base 36 of coupling member 6. For illustrative purposes, the fixation nut 8 including washer 54 is shown engaged with the coupling member 6. Subsequently, the fixation nut 8 is rotated in a predetermined direction, e.g., a clockwise direction, about the threaded post 14a. In one particular embodiment, a screwdriver (or other suitable device) is utilized to engage the slot 17 to facilitate rotation the mounting plate 4 and/or fixation nut 8. Rotation of the fixation nut 8 about the threaded post 14b causes the coupling member 6 and the mounting plate 4 to move toward one another and into secured engagement with an interior and exterior surface, respectively, of the skull of a patient. As a result thereof, the occiput is "sandwiched" between the surgical rod coupling member 6 (with barbs 20e-20g) and mounting plate 4 (with barbs 20a-20b) by threading the fixation nut 8 over the threaded post 14a and tightening to the specified torque.

In some surgical scenarios, the occiput is "sandwiched" between the surgical rod coupling member 6 (with barbs 20e-20g) and mounting plates 4 and 5 (with barbs 20a-20d) by threading the fixation nut 8 over the threaded post 14a and tightening to the specified torque.

Thereafter, the surgical rod "R" is coupled to the offset extension 34 of the coupling member 6 and secured to the coupling member 6 via the set screw 42.

As can be appreciated, the combination of the unique mounting plate 4 having the threaded post 14a configured to couple to the coupling member 6 reduces and/or eliminates the likelihood of the occipital fixation assembly 2 inadvertently pulling out from the occiput, which, in turn, reduces the risk for cerebellar injury. Moreover, anchoring the barbs 20a-20b and the barbs 20e-20g into the interior and exterior surfaces, respectively, of the skull diminishes the likelihood of inadvertent rotation of mounting plate 4 and coupling member 6 after the surgical rod "R" has been attached to the occipital fixation assembly and/or the spine.

Figure 8A:
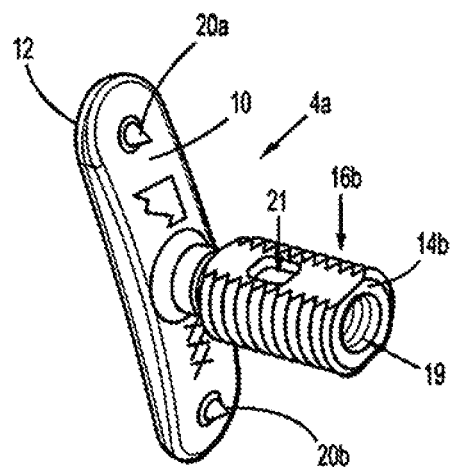
FIG. 8A is a perspective view of an alternative embodiment of a threaded post that may be utilized with the occipital fixation assembly depicted in FIG. 1.
Figure 8B:
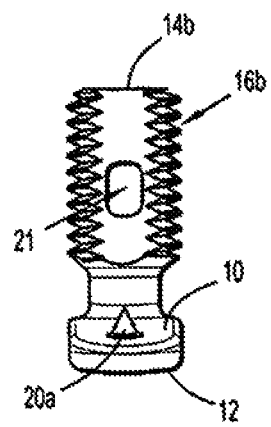
FIG. 8B is a side view of the threaded post depicted in FIG. 8A.
Figure 9:
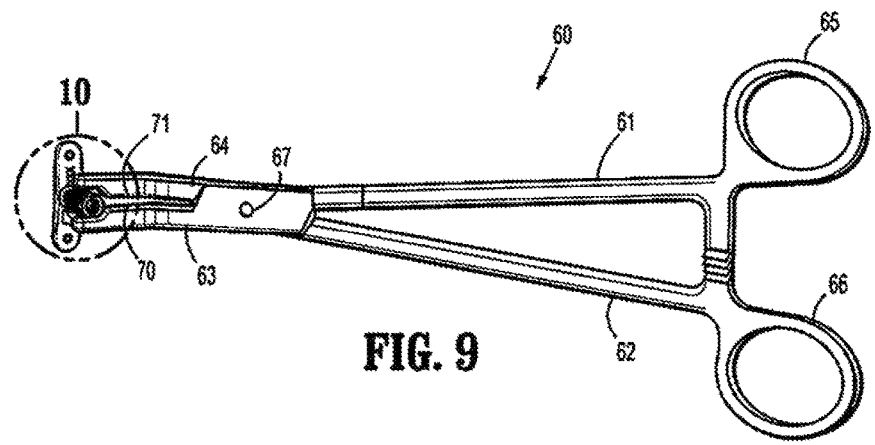
FIG. 9 is a perspective view of a surgical instrument grasping the threaded post depicted in FIG. 8A.

With reference to FIGS. 8A and 8B, an alternate embodiment of an elongated post is designated elongated post 14b. In this embodiment, the elongated post 14b is provided without the slot 17. More particularly, unlike the elongated post 14a, elongated post 14b includes a plurality of non-continuous threads 16b extending partially along an outer circumferential surface of the elongated post 14b. A proximal end of the elongated post 14b includes a threaded aperture 19 that extends into the threaded post 14b (FIG. 8A). The threaded aperture 19 is configured to receive one end of a surgical device, e.g., wrench assembly 80, for positioning and turning the fixation nut 8 about the threaded post 14b (FIGS. 11A-11D). A non-threaded aperture 21 extends traverse to the threaded aperture 19 and is configured to receive one end of a surgical device, e.g., a forceps 60, for grasping the threaded post 14b and maintaining the mounting plate 4a in a non-rotatable state when the fixation nut 8 is rotated about the elongated post 14b (FIGS. 9-11B).

Figure 10:
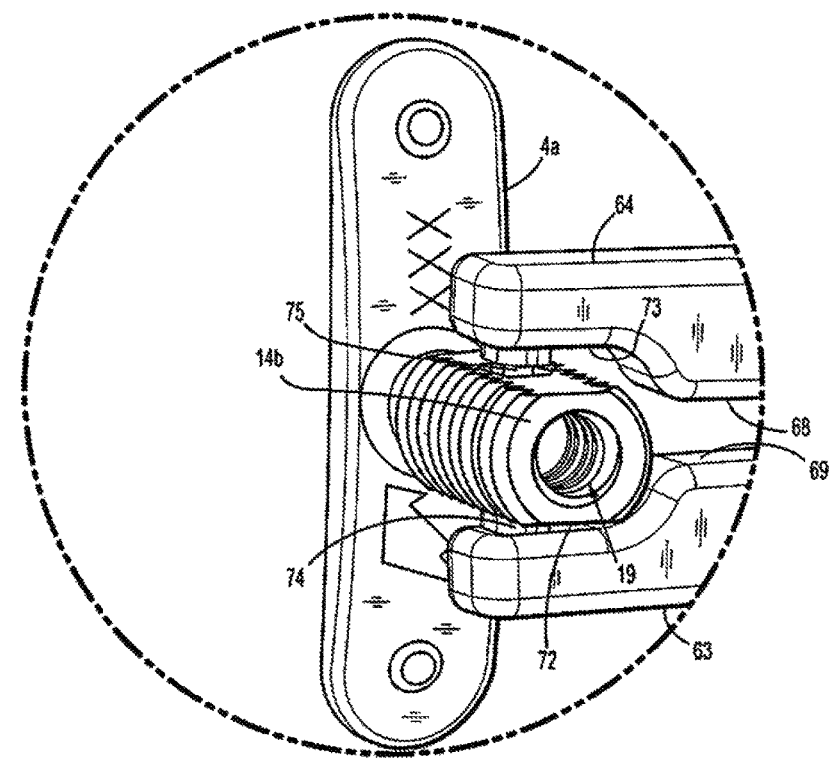
FIG. 10 is an enlarged area of detail depicted in FIG. 9.

With reference to FIGS. 9-11D, system 100 includes a forceps 60 (FIGS. 9 and 11A-11C), a wrench assembly 80 (FIGS. 11A-11D) and the occipital fixation assembly 2b (FIG. 11D) that includes the mounting plate 4a with the threaded post 14b (FIG. 10).

Forceps 60 is configured to grasp a portion of the threaded post 14b (as best seen in FIG. 10). More particularly, the forceps 60 may be utilized to grasp the threaded post 14b to facilitate positioning the mounting plate 4 within the aperture created within the sinus cavity adjacent a rear portion of a skull of a patient, i.e., the occiput. Moreover, and as noted above, forceps 60 may be utilized to grasp the threaded post 14b to maintain the mounting plate 4a in a non-rotatable state when the fixation nut 8 is rotated about the elongated post 14b. Forceps 60 includes first and second shafts 61 and 62. Each shaft 61 and 62 has a respective jaw member 63 and 64 extending from a distal end thereof and a handle 65 and 66 disposed at a proximal end thereof for effecting movement of the jaw members 63 and 64 relative to one another about a pivot 67. The jaw members 63 and 64 are movable from a first position (FIG. 11C) wherein the jaw members 63 and 64 are disposed in spaced relation relative to one another to a second position wherein the jaw members 63 and 64 cooperate to grasp the threaded post (FIGS. 9-11B).

Each of the jaw members 63 and 64 includes a respective inner facing surface 69 and 68 (FIGS. 10 and 11C) having a respective proximal end 70 and 71 (FIG. 9) and a respective distal end 72 and 73 that is offset from the proximal end 70 and 71 (FIG. 10). In the closed configuration, the distal ends 72 and 73 of the inner facing surfaces 69 and 68 remain spaced-apart from each other to facilitate grasping the threaded post therebetween (FIGS. 9-11A).

The distal ends 72 and 73 of the jaw members 63 and 64 include a protrusion 74 and 75 (FIGS. 10 and 11C) thereon that is configured to releasably engage the non-threaded aperture 21 on the threaded post 14b.

A ratchet mechanism 90 may be operably coupled to the shafts 61 and 62 adjacent the handles 65 and 66 and is configured to maintain the jaw members 63 and 64 in one or more positions. More particularly, each shaft 61 and 62 includes a respective ratchet component 90a and 90b each having a plurality of ratchet teeth that are configured to matingly engage with one another.

As can be appreciated, in the instance where the occipital fixation assembly 2 includes a mounting plate 4 with a threaded post 14a, the inner facing surfaces 69 and 68 of the forceps 60 may be provided without the protrusions 74 and 75. For example, the inner facing surfaces 69 and 68 of forceps 60 may include one or more slots or grooves that are configured to matingly engage with the plurality of threads 16a on the threaded post 14a.

Figure 11A:
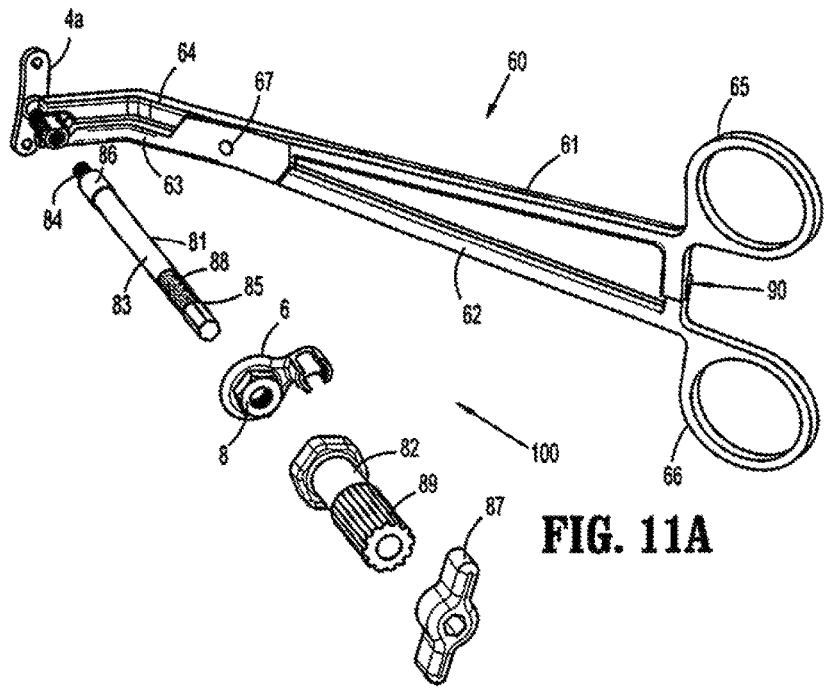
FIGS. 11A-11D are perspective views illustrating an occipital fixation system and method for attaching the occipital fixation assembly to a patient for subsequent attachment of a surgical rod thereto.
Figure 11B:
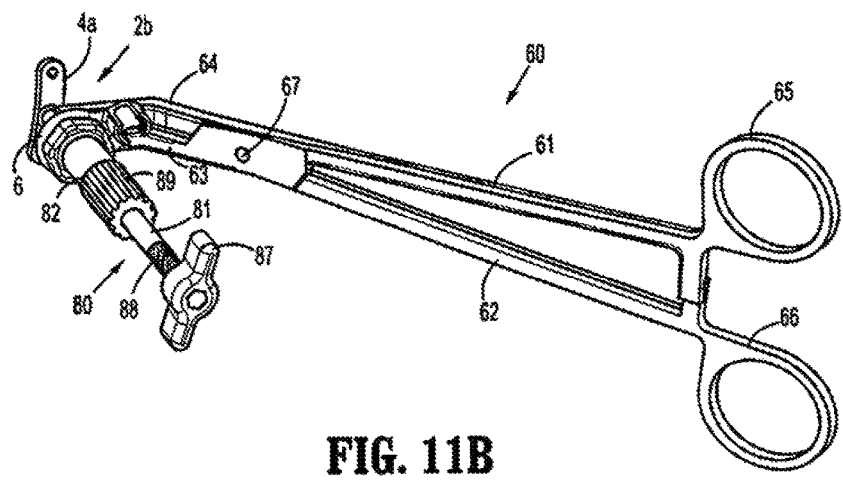
Figure 11C:
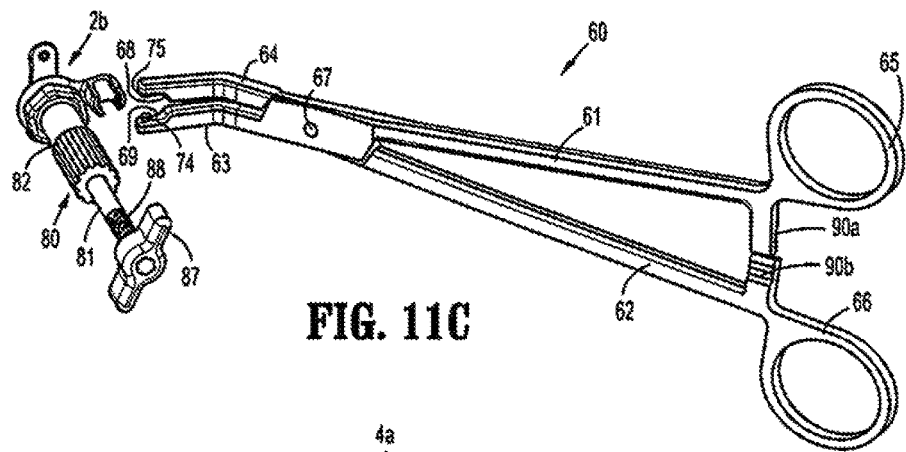

Wrench assembly 80 is configured to rotate the fixation nut 8 about the threaded post 14b (FIGS. 11B and 11C). Wrench assembly 80 includes a coupling member 81 that is configured to threadably engage the threaded aperture 19 on the threaded post 14b of the mounting plate 4 (FIGS. 11A-11C). Wrench assembly 80 includes a wrench head member 82 that is selectively and coaxially engageable with the coupling member 81 (FIGS. 11A-11C).

The coupling member 81 includes a generally elongated shaft 83 (FIGS. 11A and 11D) having a threaded distal end 84 (FIGS. 11A and 11C), and proximal end 85 that is configured to rotate the threaded distal end 84 into the threaded aperture 19 of the threaded post 14b of the mounting plate 4a for securement of the coupling member to the mounting plate 4.

A portion 86 (FIGS. 11A and 11D) of the coupling member 81 proximate to the threaded distal end 84 has an outer diameter that is slightly smaller than an inner diameter of the fixation nut 8, so that the fixation nut 8 can slide over portion 86. The portion 86 is configured to facilitate positioning the fixation nut 8 on the threaded post 14b of the mounting plate 4a. More particularly, the portion 86 is configured to guide the fixation nut 8 into position on the threaded post 14b. In one particular embodiment, the elongated extension 50 of the fixation nut 8 is configured to slide over the portion 86 and guide the fixation nut 8 into position on the threaded post 14b.

The proximal end 85 of the coupling member 81 is complementary shaped to receive an open end of a turn-key 87. In the illustrated embodiment, the proximal end 85 and the open end of the turn-key 87 include a hexagonal shape. The turn-key 87 is configured to facilitate rotation of the threaded distal end 84 into the threaded aperture 19 on the threaded post 14b of the mounting plate 4a.

In the embodiment illustrated in FIGS. 11A-11D, a portion 88 of the shaft 81 proximate to the threaded distal end 84 is textured or otherwise treated to provide an additional gripping surface for a user, or to provide mechanical interface for maintaining the turn-key 87 at the proximal end 85.

The wrench head member 82 is configured to releasably engage the fixation nut 8 and rotate the fixation nut 8 about the threaded post 14b of the mounting plate 4a. To this end, the wrench head member 82 is complementary shaped to receive and turn the fixation nut 8. In the embodiment illustrated in FIGS. 11A-11D, a proximal end 89 of the wrench head member 82 is textured or otherwise treated to facilitate rotation of the wrench member head. As can be appreciated, the wrench head member 82 may be utilized to rotate the fixation nut 8 about the threaded post 14a.

Operation of the system 100 including the occipital fixation assembly 2b including the mounting plate 4a with the threaded post 14b is described in terms of use of a method for attaching the occipital fixation assembly 2b for subsequent attachment of a surgical rod "R" thereto.

An aperture is created within a sinus cavity adjacent a rear portion of a skull of a patient. For purposes herein, the aperture may be created utilizing one or more suitable surgical devices, e.g., a surgical drill.

The forceps 60 may be utilized for grasping the threaded post 14b to insert the mounting plate 4a through the aperture created within the sinus cavity and to temporarily hold the threaded post 14b in place (FIGS. 9-11B). Thereafter, coupling member 6 is positioned about the threaded post 14b.

The fixation nut 8 including the washer 54 is positioned about the threaded post 14b and over the base 36 of coupling member 6. To facilitate positioning the fixation nut 8 about the threaded post 14b, the coupling member 81 of the wrench assembly 80 may be coupled to the threaded post 14b, see FIG. 11A where the coupling member 81 is shown adjacent the threaded post 14b just before coupling the coupling member 81 to the threaded post 14b. The turn-key may be utilized to facilitate turning the coupling member 81 about the threaded post 14b.

Subsequently, the fixation nut 8 is rotated in a predetermined direction, e.g., a clockwise direction, about the threaded post 14b. To facilitate rotating the fixation nut 8 about the threaded post 14b, the wrench head member 82 may be positioned coaxially about the coupling member 81 and into engagement with the fixation nut 8 (FIG. 11B). It should be noted that once the fixation nut 8 has been engaged to the threaded post 14b, the forceps 60 may be removed from engagement with the threaded post 14b (FIG. 11C). It is further contemplated that the threaded engagement between to threaded distal end 84 and the threaded aperture 19 may be opposed to the threaded engagement between fixation nut 8 and post 14b (i.e., one may engage in a clockwise direction and the other in a counterclockwise direction) so that as the fixation nut 8 is tightened the coupling member 81 does not loosen from the threaded post 14b. In this manner, even after the forceps 60 have been removed, control may be exerted over the threaded post 14b as the fixation nut 8 is tightened.

The wrench head member 82 is rotated about the fixation nut 8, which, in turn, rotates the fixation nut 8 about the threaded post 14b, this in turn, causes the coupling member 6 and the mounting plate 4a to move toward one another and into secured engagement with an interior and exterior surface, respectively, of the skull of a patient.

Figure 11D:
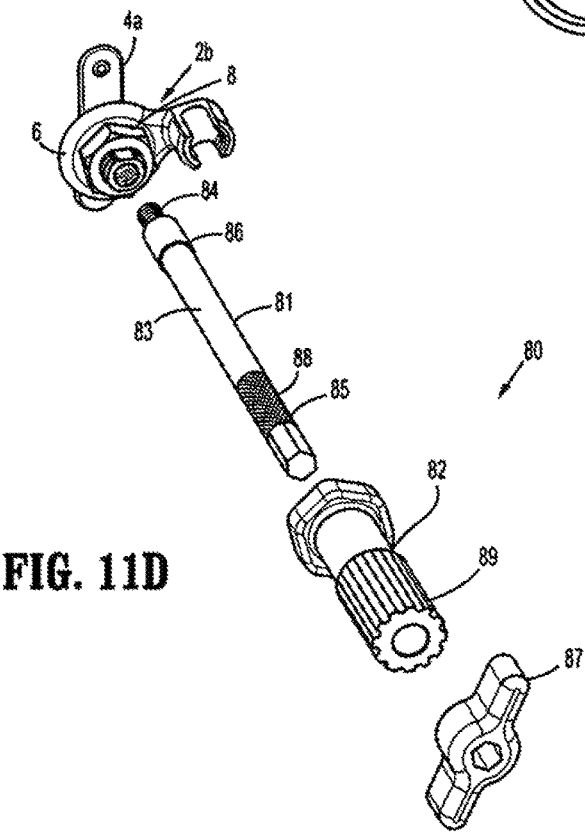

In one surgical scenario, after the coupling member 6 and the mounting plate 4a are moved into secured engagement with the interior and exterior surface of the skull, the wrench assembly 80 is removed from the occipital fixation assembly 2 (FIG. 11D). Thereafter, the surgical rod "R" is coupled to the offset extension 34 of the coupling member 6 and secured to the coupling member 6 via the set screw 42.

From the foregoing and with reference to the various figure drawings, those skilled in the art will appreciate that certain modifications can also be made to the present disclosure without departing from the scope of the same. For example, in some embodiments the slot 38 of the offset extension 34 includes a taper locking mechanism for capturing the surgical rod "R" such that a set screw 42 is not required.

In yet another embodiment, the slot 38 of the offset extension 34 includes a polyaxial coupling for capturing the surgical rod "R" such that an angle and trajectory of the surgical rod "R" does not limit the position of the occipital fixation assembly 2.

Figure 12A:
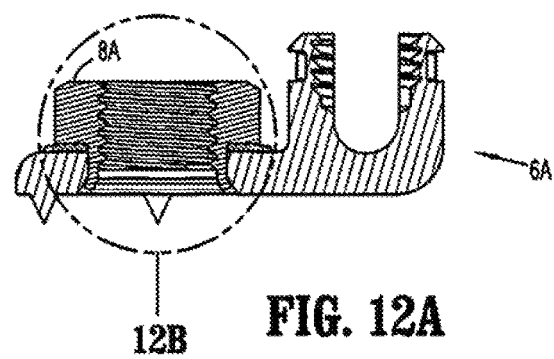
FIG. 12A is a cross-sectional view of a coupling member according to another embodiment of the present disclosure.
Figure 12B:
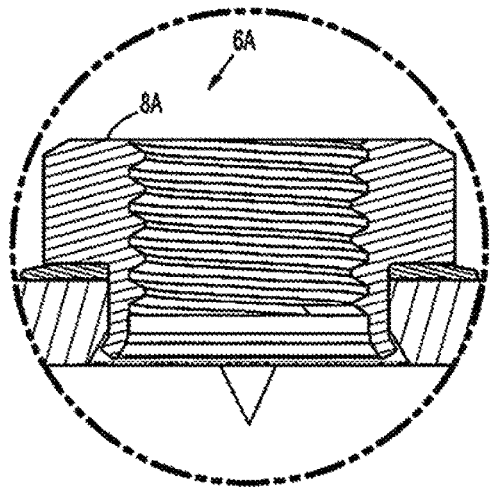
FIG. 12B is the enlarged area of detail depicted in FIG. 12A.

In yet another embodiment, a fixation nut may be integrally formed with a coupling member. More particularly, and with reference to FIGS. 12A and 12B, a coupling member 6A and a fixation nut 8A are integrally formed with one another via one or more suitable coupling methods, e.g., soldering, brazing or welding. In this instance, the fixation nut 8A is swaged, but rotatable, to the coupling member 8A along with a washer making it an integral assembly. In this instance, the coupling member 6A including the fixation nut 8A are positioned about the threaded post 14b simultaneously.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. An occipital fixation system, comprising:
   an occipital fixation assembly, including:
      a first mounting plate configured for placement within a sinus cavity adjacent a rear portion of a skull of a patient, the first mounting plate having a threaded post extending therefrom, a non-threaded portion of the threaded post defining a non-threaded relief therein;
      a coupling member including an aperture configured to receive the threaded post therethrough, the coupling member including an offset extension disposed in parallel orientation with respect to the threaded post and configured to support a surgical rod thereon; and
      a fixation nut configured to threadably engage the threaded post, the fixation nut rotatable about the threaded post and translatable therealong, the fixation nut rotatable with respect to the first mounting plate and the coupling member such that rotation of the fixation nut in a predetermined direction brings the first mounting plate and the coupling member toward one another and into secured engagement with the skull of the patient;
   a forceps configured to grasp the non-threaded relief of the threaded post to facilitate positioning of the first mounting plate through an aperture that has been previously drilled into the sinus cavity; and
   a wrench assembly configured to engage and, subsequently, rotate the fixation nut about the threaded post.

2. The occipital fixation system according to claim 1, wherein a first barb is operably disposed on a top surface of the first mounting plate and a second barb is operably disposed on a bottom surface of the coupling member.

3. The occipital fixation system according to claim 2, wherein the first and second barbs are configured to anchor into an inside of the skull and outside of the skull, respectively, to minimize respective rotation of the first mounting plate and coupling member when the fixation nut is rotated about the threaded post.

4. The occipital fixation system according to claim 1, wherein a washer is disposed between the fixation nut and the aperture on the coupling member and serves as a lock washer, wherein a bottom surface of the fixation nut is receivable through the washer and at least partially extends through the aperture of the coupling member, wherein the fixation nut is swaged to the coupling member making the coupling member and fixation nut an integral assembly.

5. The occipital fixation system according to claim 1, wherein the offset extension includes a generally elongated slot having a threaded portion configured to receive a set-screw therein and a non-threaded portion configured to receive the surgical rod therein, the threaded and non-threaded portions of the offset extension arranged such that when the surgical rod is secured thereto, the surgical rod is oriented perpendicular to the set-screw.

6. The occipital fixation system according to claim 1, wherein the threaded post of the first mounting plate defines an end face having a transverse slot defined therein, the slot configured to receive a portion of a screwdriver therein.

7. The occipital fixation system according to claim 1, wherein the threaded post is integral to the first mounting plate.

* * * * *